(12) United States Patent
Sakamoto et al.

(10) Patent No.: US 9,861,510 B2
(45) Date of Patent: Jan. 9, 2018

(54) CERVICAL ORTHOSIS

(71) Applicants: REHABITECH Co., LTD., Kyoto (JP); RAKUHOKUGISHI, PROSTHETIC AND ORTHOTIC MANUFACTURING Co., LTD., Kyoto (JP)

(72) Inventors: Tsutomu Sakamoto, Kyoto (JP); Akinobu Sakamoto, Kyoto (JP); Takeshi Hanajima, Kyoto (JP); Ban Masuhara, Kyoto (JP); Masaya Nomura, Kyoto (JP); Kanji Mori, Otsu (JP)

(73) Assignees: Rakuhokugishi Prosthetic and Orthotic Manufacturing Co., Ltd., Kyoto-fu (JP); Rehabitech Co., Ltd., Kyoto-fu (JP)

( * ) Notice: Subject to any disclaimer, the term of this patent is extended or adjusted under 35 U.S.C. 154(b) by 0 days.

(21) Appl. No.: 13/919,468

(22) Filed: Jun. 17, 2013

(65) Prior Publication Data

US 2014/0371645 A1     Dec. 18, 2014

(51) Int. Cl.
*A61F 5/055*     (2006.01)
*A61F 5/058*     (2006.01)

(52) U.S. Cl.
CPC .......... *A61F 5/055* (2013.01); *A61F 5/05883* (2013.01)

(58) Field of Classification Search
CPC ...... A61F 5/00; A61F 5/01; A61F 5/02; A61F 5/022; A61F 5/05; A61F 5/055; A61F 5/05883
USPC ..................................................... 602/17–19
See application file for complete search history.

(56) References Cited

U.S. PATENT DOCUMENTS

| | | | | |
|---|---|---|---|---|
| 4,502,471 A * | 3/1985 | Owens | .................... | A61F 5/055 602/18 |
| 4,708,129 A * | 11/1987 | Pujals, Jr. | ............... | A61F 5/055 128/DIG. 23 |
| 5,097,824 A * | 3/1992 | Garth | ...................... | A61F 5/055 128/DIG. 23 |
| 5,575,763 A * | 11/1996 | Nagata | .................... | A61F 5/055 128/875 |
| 6,267,741 B1* | 7/2001 | Lerman | .......................... | 602/18 |
| 6,494,854 B1* | 12/2002 | Visness | ................... | A61F 5/055 128/DIG. 23 |
| 2010/0268138 A1* | 10/2010 | Summit et al. | ................. | 602/16 |

FOREIGN PATENT DOCUMENTS

JP        6-3311        1/1994

* cited by examiner

*Primary Examiner* — Keri J Nelson
(74) *Attorney, Agent, or Firm* — Norris McLaughlin & Marcus, P.A.

(57) ABSTRACT

A cervical orthosis comprises a main body supporting member having an occipital region supporting part; and a plurality of belt-like members for fixing the main body supporting member to a human body. An occipital region receiving member is fixed inside the occipital region supporting part at the positions near a temporal part at a predetermined interval from a curved surface of the occipital region supporting part, whereby the occipital region receiving member is deformed according to the shape of an occipital region and a pressure is distributed when the patient is in the supine posture.

1 Claim, 5 Drawing Sheets

CERVICAL ORTHOSIS

BACKGROUND OF THE INVENTION

The present invention relates to a cervical orthosis, and more specifically, the cervical orthosis which stably holds an occipital region when medically treating a cervical spine disease or injury so that a cervical spine can be held in a correct posture.

In a well-known conventional cervical orthosis which has been developed to correct a posture of a cervical spine into a neutral position, a front supporting body having a chin-placing part and a supporting body formed to receive an occipital region are fixed to each other by a belt, and are further fixed to a frontal region of a head by a belt arranged on an occipital region supporting part so that a head posture can be held stably.

A conventional art of the cervical orthosis of the type which supports the occipital region like the above-mentioned is shown in the following document, for example: Japanese Unexamined Utility Model Application Publication No. 1994-3311.

The supporting body of the cervical orthosis like the above-mentioned, which is usually formed of a hard synthetic resin, is placed on the back and fixed to a human body by a belt. An occipital region supporting part on the upper part of the supporting body is also formed of the synthetic resin in an integrated manner, and is formed to have a curve to properly receive the occipital region. The occipital region supporting part is provided with a belt-like body, which is configured to be wound around a frontal region to firmly fix a head.

SUMMARY OF THE INVENTION

A stable posture is maintained by fitting the occipital region to the occipital region supporting part having a curved shape. However, when a patient of a cervical spine disease under medical treatment lies on the back and the heavy head is supported, pressure may locally concentrate on part of the occipital region supporting part depending on the shape of the individual head and the supine posture.

As a result, the patient comes to have a pain on the head even after a comparatively short time, and sleep is disturbed.

To solve the problem, measures for alleviating the load concentration have been taken. Namely, a cushioning material is bonded to the inside of the occipital region supporting part to receive the head.

However, since the head is very heavy, the patient feels that the cushioning material is locally compressed and that the occipital region is directly supported by the occipital region supporting part depending on the shape of the head or the supine posture even when the cushioning material made of sponge, felt or the Eke is arranged, and the patient feels a pain.

In the meantime, the thickness of the cushioning material could be increased, however, it has been found that the increase in the thickness is not preferable because the thickness that can distribute the load of the head leads to unstableness of the head posture, rather, and also air permeability is spoiled.

In view of the above-mentioned problem, a purpose of the present invention is to stabilize the head posture to medically treat the cervical some disease while avoiding generation of pain on the occipital region even in the supine posture, in the above-mentioned cervical orthosis.

To achieve the above-mentioned purpose, the cervical orthosis of the present invention including: a main body supporting member (1) formed by molding a synthetic resin and in a manner of extending from the back region to the occipital region to receive the occipital region and to stabilize the posture so that the cervical spine can be protected; and a plurality of belt-like members (2) for fixing the main body supporting member (1) to a patient's body, of which an occipital region supporting part (1A) of the main body supporting member (1) is formed to have a curve that surrounds the occipital region, and a cushioning material (3) directly coming into contact with the occipital region is arranged on the occipital region supporting part (1A), wherein an occipital region receiving member (4) is arranged inside the occipital region supporting part (1A) at a predetermined interval from a curved surface (1a) of the occipital region supporting part (1A), the occipital region receiving member (4) is fixed to the occipital region supporting part (1A) at positions near a temporal region, and the occipital region receiving member (4) is formed of a deformable material so that it may receive an unevenly applied pressure in a distributed manner without pressure concentration caused by the shape of the occipital region or posture displacement.

The cervical orthosis referred to in this invention is what is fitted to a human body, or in particular, to the back to support a head in a correct posture and to correct a cervical spine into a right posture (state of arrangement) so that a cervical spine disease can be medically treated. Needless to say, combination with the cervical orthosis for placing a chin is also included.

Further, the main body supporting member (1) is basically embodied by forming the same with a synthetic resin, however, FRP, metal or other materials having sufficient strength can also be used.

In addition, the cushioning material (3) may be formed of a foamed resin like urethane, non-woven fabric, or other materials which are generally used as a cushioning material.

According to a conventional cervical orthosis, when a patient of a cervical spine disease who is under medical treatment wearing the conventional cervical orthosis lies on the back, the load of a head (the weight of the head itself) is locally and unevenly applied to the occipital region supporting part receiving the occipital region due to the head posture, head shape or the like, causing a pain on part of the occipital region. However, according to the cervical orthosis of the present invention, an occipital region receiving member arranged at an interval from the occipital region supporting part receives the load in a distributed manner without load concentration which may be caused by posture displacement. Thus, by avoiding local load concentration on the occipital region, the pain is prevented, which is a noticeable effect, and medical treatment on the cervical spine disease can be continued even when the patient lies in the supine posture.

In the meantime, the cushioning material is used also in the present invention. The cushioning material is to fulfill a buffering function for softly receiving the occipital region but not to fulfill the function of distributing the above-mentioned locally applied load of the weight of the head itself.

Other effects of this invention will be clarified in the following description of embodiments.

According to a preferred embodiment of this invention, a main body supporting member (1) is integrally formed of a synthetic resin, and a cushioning material (3) is detachably fitted to an occipital region receiving member (4) by a plurality of hook and loop fasteners (5).

According to this configuration, manufacturing is facilitated due to the integral formation. Further, attaching and detaching of the cushioning material (3) is also facilitated, and the cushioning material (3) directly in contact with the occipital region is easily replaced, improving sanitary care like cleaning.

It is preferable that the occipital region receiving member (4) is fitted to an occipital region supporting part (1A) of the main body supporting member (1) by rivets.

This configuration makes it easier to replace the occipital region receiving member (4) with the one having different softness or the one having the shape which is better fitted to the occipital region of a specific patient, since the replacement is performed only by releasing the rivets.

Further, it is preferable that the occipital region receiving member (4) made of a thin synthetic resin is formed into a substantially grid-like shape in planar view, and is configured to be deformable according to the pressure unevenly applied to the occipital region.

This configuration enables the occipital region receiving member (4) to be manufactured at a low cost, and the substantially grid-like shape is easier to be elastically deformed due to the structural characteristic thereof.

In the present invention, polyethylene is used as the synthetic resin for manufacturing the occipital region receiving member (4). The main body supporting member (1) is also made of polyethylene, and is formed to be thick, i.e., to have a thickness of around 5 mm, by which sufficient rigidity is imparted. On the other hand, the occipital region receiving member (4) is formed to be thinner to have a thickness of around 2 mm and is formed into a grid-like shape having bands of around 4 mm in width, by which flexibility is imparted.

Further, the occipital region receiving member (4) is preferably formed into a net-like shape using a woven, non-woven or knitted fiber material, and is formed to be deformable according to the pressure unevenly applied to the occipital region. Needless to say, the cushioning material is used also in this case.

Due to the net-like shape, the form of the occipital region receiving member (4) is more easily changed so that the same can be better adapted to the occipital region and a supine posture, compared to the one made of the synthetic resin, which is an advantage.

DETAILED DESCRIPTION OF THE INVENTION

Preferred embodiments of the cervical orthosis according to the present invention will be described in detail hereinafter referring to drawings. As shown in FIGS. 1 to 9, the cervical orthosis which is to be detachably fitted to a back region or a chest region by belts basically comprises a main body supporting member 1 extending from the hack region to an occipital region to stabilize a posture by receiving the occipital region and to protect a cervical spine; and a plurality of belt-like members 2 fixing the main body supporting member 1 to a human body. An occipital region supporting part 1A of the main body supporting member 1 is formed to have a curve in a manner of surrounding the occipital region. A cushioning material 3 directly coming into contact with the occipital region is arranged on the occipital region supporting part 1A.

Figure 1:
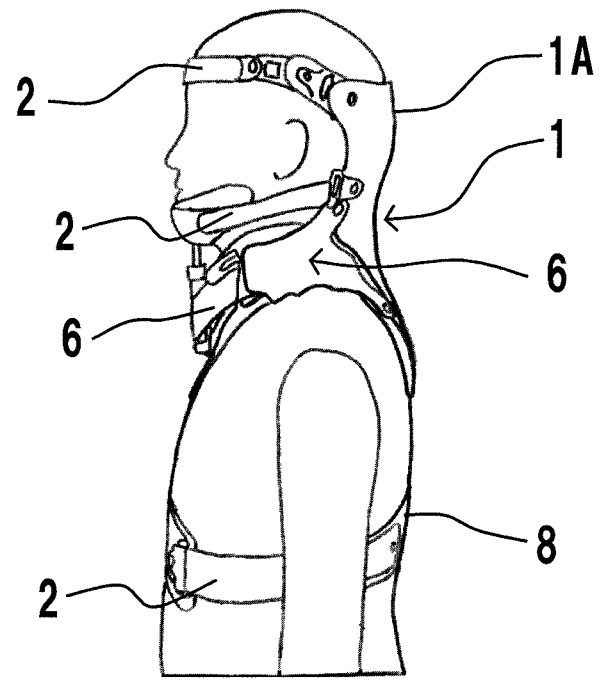
FIG. 1 is a side view of a cervical orthosis of this invention which is fitted to a human body.
Figure 2:
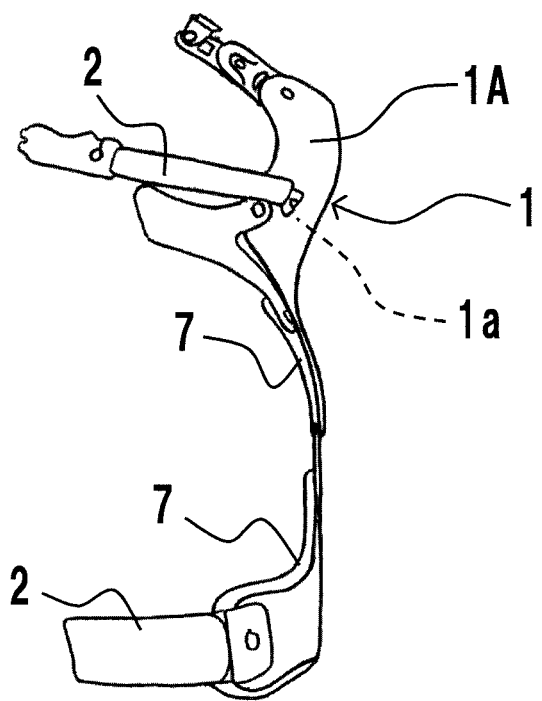
FIG. 2 is a side view of the cervical orthosis.
Figure 3:
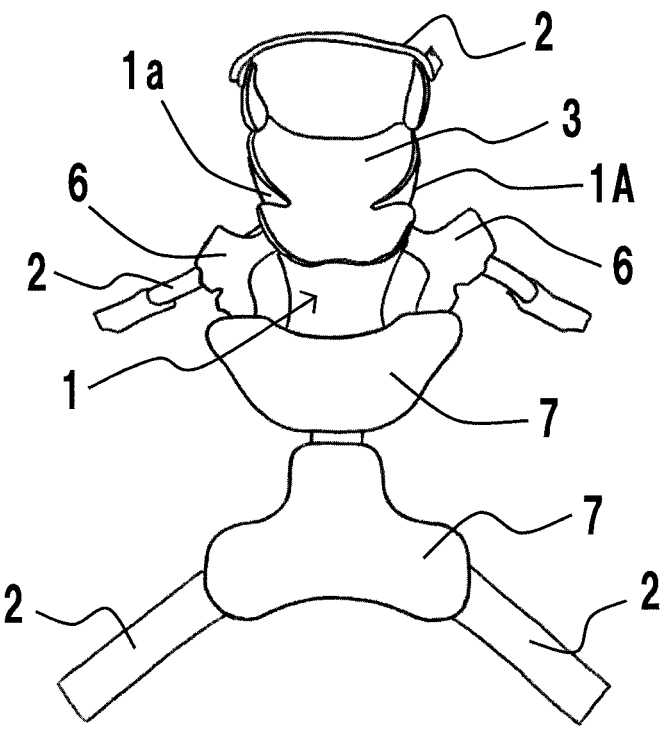
FIG. 3 is a front view of the cervical orthosis.

As shown in FIG. 1, the occipital region supporting part 1A is formed to receive a lower part of the occipital region including the part which is a little higher than a rear edge of the occipital region. However, to what extent the occipital region supporting part 1A covers may be determined arbitrarily. As for covering of a temporal region, the occipital region supporting part 1A is formed to cover to the back of ears, in this embodiment. However, to what extent the occipital region supporting part 1A covers may also be determined arbitrarily. As shown in the drawing, the occipital region supporting part 1A of the main body supporting member 1, and the part extending downward, in other words, the part corresponding to a shoulder region are formed in an integrated manner. However, the occipital region supporting part 1A and the lower part (the part corresponding to the shoulder region and the back region) can be formed into separate bodies, and be connected to each other with a rigid member like an aluminum alloy. In other words, the main body supporting member 1 is provided with at least the occipital region supporting part 1A.

As shown in FIG. 1 etc., the belt-like members 2 are wound and fastened around a frontal region, a chin, a cervical region, and a chest region. The fastening structure is materialized by an engaging-type fastener with a length-adjustable function, which is generally used in this kind of fasteners. Since the fastener has a known structure, detailed explanation is not given here. The belt-like members 2 are directly fitted to the main body supporting member 1 by rivets in a rotatable manner, or an appropriate bracket made of a resin.

The main body supporting member 1 is a molded product of polyethylene, and is configured to have a thickness of around 5 mm to exert sufficient strength. The occipital region supporting part 1A is curved to have a recess on an inside thereof, and the parts thereof corresponding to the shoulder region and the cervical region are curved so that they can substantially fit to a human body.

Polyethylene is used to form the main body supporting member 1 in this embodiment. However, PP (polypropylene), PET (polyethylene terephthalate), POM, an ABS resin, etc. can also be used. When need arises, a lightweight aluminum alloy or other metal materials can also be used for molding of the main body supporting member 1.

As for the cushioning material 3, a material which is configured by sewing urethane foam and a non-woven fabric together to have a thickness of around 5-10 mm is used in this embodiment. A rear surface of the cushioning material 3, in other words, a side thereof facing the occipital region supporting part 1A is configured with the non-woven fabric and is provided with a surface which can be engaged with hook and loop fasteners. Hook and loop fasteners 5 are attached to a plurality of corresponding positions of an occipital region receiving member 4, which are four positions in this embodiment and will be described, later, and the position of the cushioning material 3 is fixed by means of engagement. When the cushioning material 3 is configured with other materials, fasteners are attached to a surface thereof.

According to this invention, the occipital region receiving member 4 is arranged inside the occipital region supporting part 1A at a predetermined interval from a curved surface 1a of the occipital region supporting part 1A. The occipital region receiving member 4 is fixed to the occipital region supporting part 1A at four positions near a temporal region. The occipital region receiving member 4 is formed of a deformable material so that the uneven pressure which may be caused by the posture displacement of the occipital region can be received in a distributed manner without being concentrated.

Figure 7:
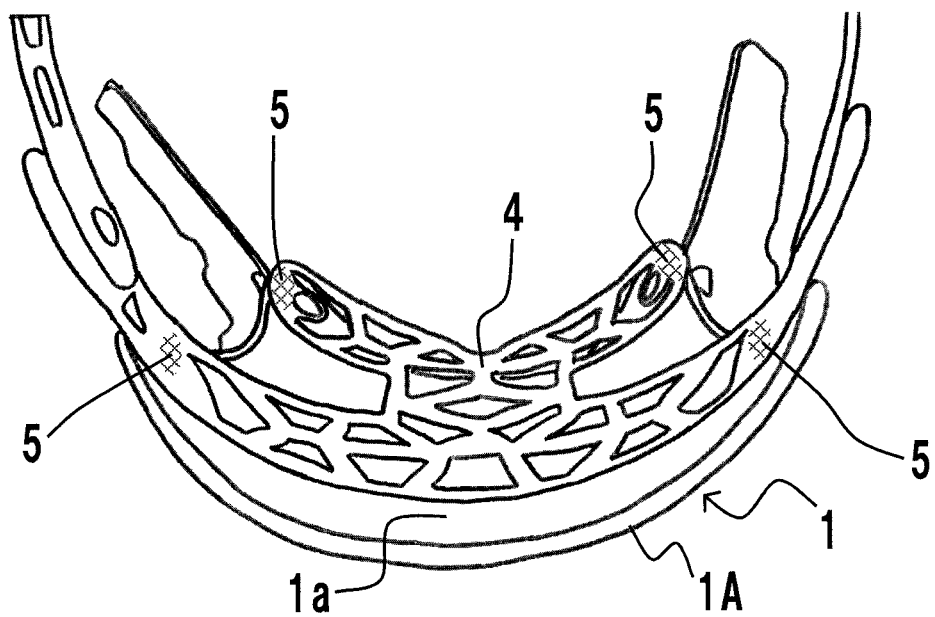
FIG. 7 is an enlarged planar view showing an occipital region receiving member which is exposed by removing the cushioning material of the cervical orthosis.
Figure 8:
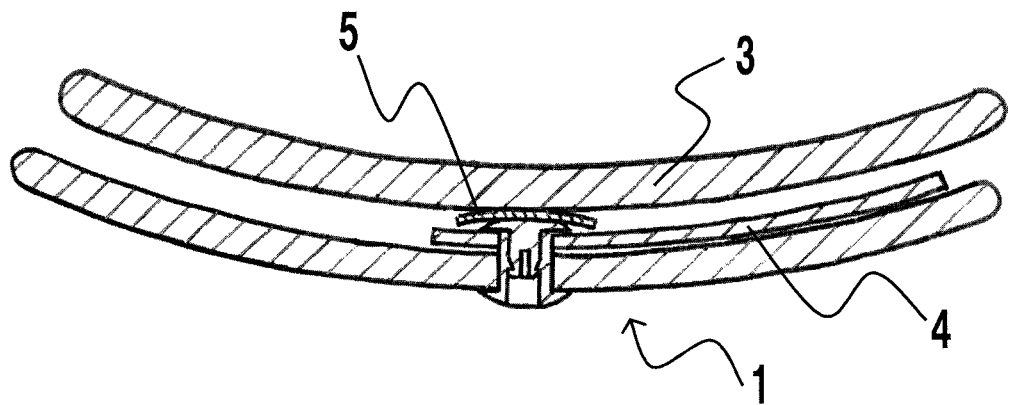
FIG. 8 is an enlarged sectional view of the cervical orthosis sectioned along a line A-A of FIG. 6.

The predetermined interval between the occipital region receiving member 4 and the curved surface 1a of the occipital region supporting part 1A is set to be largest, i.e. about 15 mm, at the part between the rear edge of the occipital region and the curved surface 1a so that the occipital region may not directly come into contact with the curved surface 1a when the occipital region is displaced. The interval becomes narrower gradually as it comes closer to the temporal region. As shown in FIGS. 7 and 8, the occipital region receiving member 4 comes into contact with the occipital region supporting part 1A at side edges of an upper end of the occipital region supporting part 1A, and side edges of the same near a cervical region, where the occipital region receiving member 4 and the occipital region supporting part 1A are detachably fixed together by rivets at four positions in total, in this embodiment.

Figure 4:
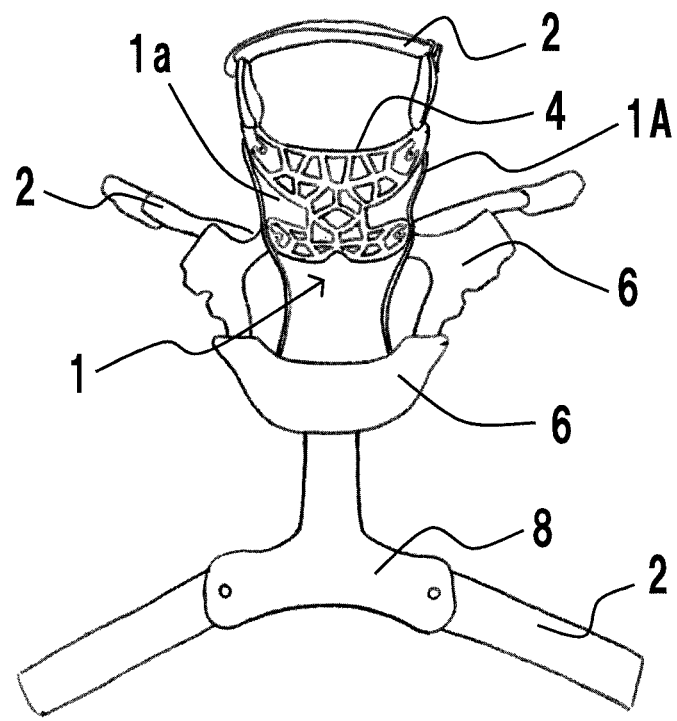
FIG. 4 is a front view of the cervical orthosis from which a cushioning material is removed.
Figure 5:
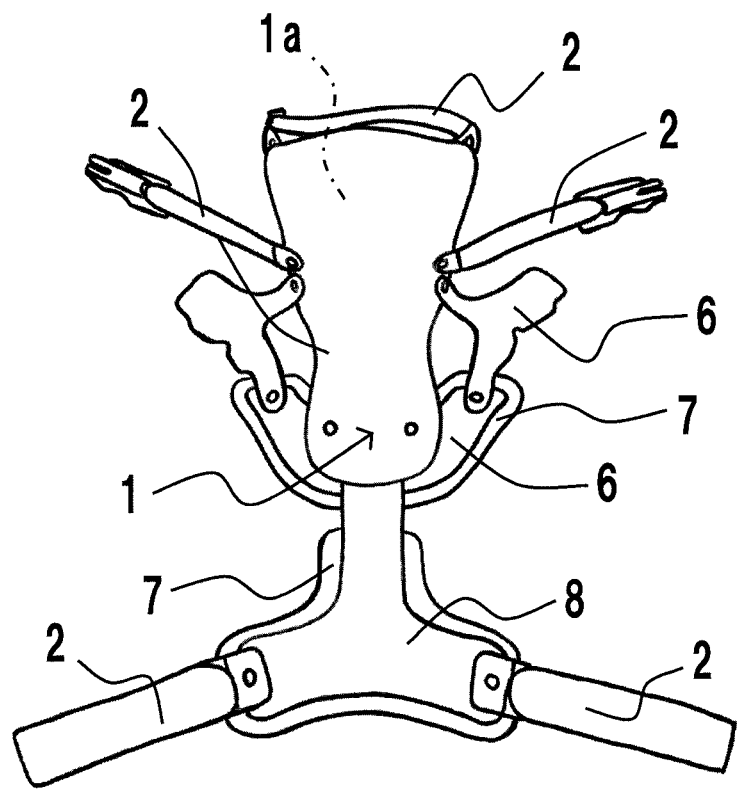
FIG. 5 is a rear view of the cervical orthosis.
Figure 6:
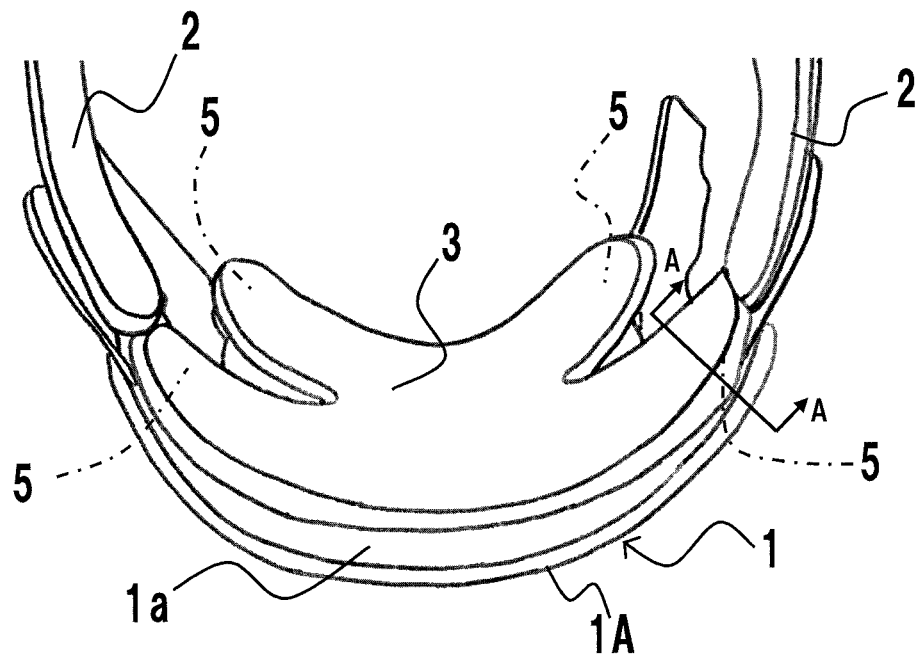
FIG. 6 is an enlarged planar view of an occipital region supporting part of the cervical orthosis.
Figure 9:
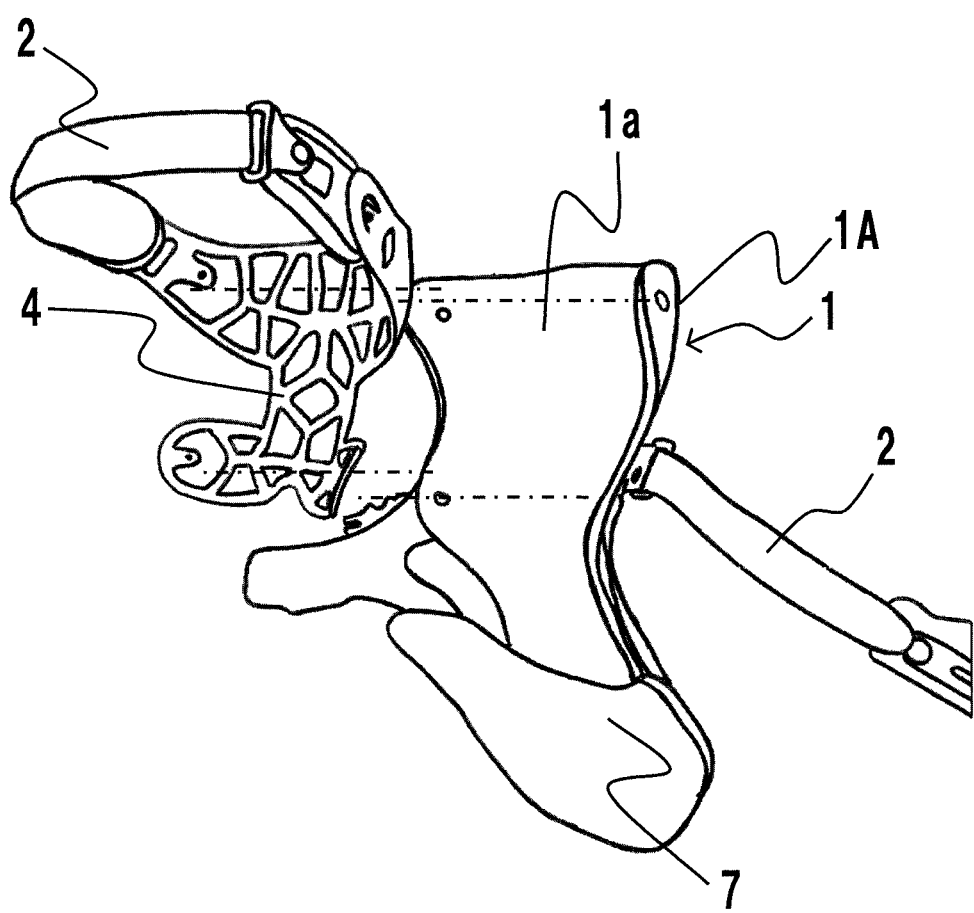
FIG. 9 is an exploded perspective view showing the state of the cervical orthosis in which the occipital region receiving member is detached from the occipital region supporting part.

As shown in FIGS. 4, 7 and 9, the occipital region receiving member 4 is formed into a substantially shape in planar view by using a thin, synthetic resin material, or in this embodiment, a polyethylene material having a thickness of 2 mm. The substantially grid like shape includes spaces of arbitrary shapes like a trapezoidal shape, a diamond shape, or a triangular shape. The occipital region receiving member 4 is configured to be deformable according to the uneven pressure applied to the occipital region. As shown in the FIGS., the grid-like occipital region receiving member 4 is formed into a T-letter shape or a shape like a cross with an underscore in an exploded front view so that it may hold most part of the occipital region.

In the meantime, as shown in FIGS. 2 to 5, an upper branch of a trifurcated member 8 formed of a similar molded synthetic resin is fixed to a lower end part of the main body supporting member 1 by rivets, and belt-like members 2 are respectively fitted to two lower branches of the trifurcated member 8. Upon use, the belt-like members 2 are wound around a chest region to partly serve for fitting to the human body.

Similarly, supporting members 6 are appropriately fitted to the main body supporting member 1 in a manner of extending from the main body supporting member 1 to support the cervical region and the chin. A pad 7 is stuck to the trifurcated member 8 or the supporting members 6.

Conventionally, when the patient wearing the cervical orthosis lies on the back, the weight of the head itself is directly applied to the curved surface 1a of the occipital region supporting part 1A depending on individual characteristics of the head shape or the like. Even when a cushioning material like a urethane or non-woven material is arranged, a load is locally applied to an occipital region giving a pain to the patient. However, according to this invention, the occipital region receiving member 4 is arranged at an interval from the curved, surface 1a of the occipital region supporting part 1A, whereby a load can be supported by the whole occipital region in a distributed manner without being locally concentrated, and the pain is prevented or alleviated.

Other forms of embodiment of the occipital region receiving member 4 are explained below without using drawings. In the above-mentioned embodiment, the occipital region receiving member 4 is formed of a molded synthetic resin (polyethylene) into a substantially grid-like shape. Instead, a fiber material like a woven, nonwoven or knitted material formed into a net-dike shape may be used, by which elastic deformation is facilitated in a predetermined range and the occipital region supporting member 4 is deformed according to the pressure unevenly applied to the occipital region while distributing the load.

The occipital region receiving member 4 formed into the net-like shape using the woven, non-woven or knitted material is flexible and adaptable to large deformation compared to the occipital region receiving member 4 made of the synthetic resin, and has higher adaptability to individual characteristics of the shape of the patient's head, whereby the expected effect is farther improved.

The cervical orthosis according to the present invention prevents the weight of an occipital region itself from concentrating when a patient lies on the back wearing the cervical orthosis, by which a correct cervical posture can be maintained for a purpose of medical treatment. Therefore, the cervical orthosis can be widely applied to patients of cervical spine injury.

We claim:
1. A cervical orthosis comprising:
a main body supporting member that is formed as a unitary structure and is made of synthetic resin having a thickness of around 5 mm, and which is configured to extend from a back region to an occipital region to cover a back portion of ears of a person wearing the cervical orthosis to protect a cervical spine by receiving the occipital region and stabilizing a posture, the main body supporting member having an occipital region supporting portion which spans-vertically and laterally and is configured to conform to anatomical curvature of the occipital spine so as to surround the occipital region;
a trifurcated member formed of molded synthetic resin fixed to a lower end portion of the main body supporting member by rivets, the trifurcated member comprising a pad comprising three branches protruding in different directions;
a plurality of belt-like members configured for fixing the main body supporting member and the bifurcated portion to a human body, wherein one of the belt-like members is attached to each of two lower branches of the trifurcated member;
a cushioning material comprising urethane foam having a thickness of 5 mm to 10 mm, and being arranged on the occipital region supporting portion and being configured for directly being in contact with the occipital region; and an occipital region receiving member made of a synthetic resin formed into a substantially grid-like shape in planar view, and having a curved shape to be configured to surround the occipital region of the person, and having a thickness of 2 mm and comprising bands having 4 mm in width, and being configured to be deformable according to the pressure unevenly applied to the occipital region, and said occipital region receiving member being arranged inside the occipital region supporting portion, being fixed to the occipital region supporting portion by rivets at four positions, and being configured to be located between the occipital region supporting portion and the occipital region in a configuration by which the occipital region supporting portion shields the occipital region receiving member from external view from behind said person;

wherein the occipital region receiving member is spaced from the occipital region supporting portion of the main body supporting member by a spacing that varies from a maximum spacing of 15 mm at a most rear point of the occipital region receiving member toward a minimum spacing toward left and right side edges of the occipital region receiving member;

wherein the cushioning material is detachably fitted to the occipital region receiving member by a plurality of hook and loop fasteners;

wherein the occipital region receiving member is configured to receive the occipital region via the cushioning material so as to support the occipital region of the head in combination with the occipital region supporting portion;

wherein the occipital region receiving member of deformable material is fixed to the occipital region supporting portion by rivets at a plurality of positions; and wherein the occipital region receiving member is configured to receive pressure, being unevenly applied to the occipital region due to a posture displacement, in a distributed manner without concentration of the pressure.

* * * * *